(12) United States Patent
Harada et al.

(10) Patent No.: US 9,169,192 B2
(45) Date of Patent: Oct. 27, 2015

(54) HYDROGENATION CATALYST, PROCESS FOR ITS PRODUCTION AND ITS USE

(75) Inventors: Tsuneo Harada, Shunan (JP); Shou Kawabe, Shunan (JP)

(73) Assignee: TOSOH CORPORATION, Shunan (JP)

( * ) Notice: Subject to any disclaimer, the term of this patent is extended or adjusted under 35 U.S.C. 154(b) by 0 days.

(21) Appl. No.: 13/518,933

(22) PCT Filed: Dec. 24, 2010

(86) PCT No.: PCT/JP2010/073414
§ 371 (c)(1),
(2), (4) Date: Jun. 25, 2012

(87) PCT Pub. No.: WO2011/078354
PCT Pub. Date: Jun. 30, 2011

(65) Prior Publication Data
US 2012/0264976 A1    Oct. 18, 2012

(30) Foreign Application Priority Data

Dec. 25, 2009  (JP) .................................. 2009-295876
Dec. 25, 2009  (JP) .................................. 2009-295877

(51) Int. Cl.
| | | |
|---|---|---|
| C07C 209/00 | (2006.01) | |
| C01B 33/24 | (2006.01) | |
| C01B 33/32 | (2006.01) | |
| C07C 209/36 | (2006.01) | |
| B01J 23/72 | (2006.01) | |
| B01J 23/78 | (2006.01) | |
| B01J 37/18 | (2006.01) | |

(Continued)

(52) U.S. Cl.
CPC .............. *C07C 209/36* (2013.01); *B01J 23/72* (2013.01); *B01J 23/78* (2013.01); *B01J 37/18* (2013.01); *B01J 21/16* (2013.01); *B01J 35/1014* (2013.01)

(58) Field of Classification Search
None
See application file for complete search history.

(56) References Cited

U.S. PATENT DOCUMENTS

| | | | |
|---|---|---|---|
| 5,955,620 | A | 9/1999 | Mercker et al. |
| 6,093,677 | A | 7/2000 | Mercker et al. |

FOREIGN PATENT DOCUMENTS

| | | |
|---|---|---|
| DE | 102 18 849 A1 | 11/2003 |
| EP | 0 827 956 A1 | 3/1998 |
| JP | 49-321 | 1/1974 |

(Continued)

OTHER PUBLICATIONS

JP-2007289855 machine translation (2007), pp. 1-23.*

(Continued)

*Primary Examiner* — Clinton Brooks
(74) *Attorney, Agent, or Firm* — Nixon & Vanderhye P.C.

(57) ABSTRACT

To provide a hydrogenation catalyst which does not contain chromium oxide, unlike conventional copper/chromium oxide catalysts, and therefore does not cause any environmental contamination or health hazard, and which shows an activity, selectivity and durability at equivalent or higher levels to or than those of conventional copper/chromium oxide catalysts. A hydrogenation catalyst which comprises, as the main components, (1) copper and (2) at least one member selected from the group consisting of silicon oxide, calcium oxide and calcium silicate, wherein the content of the copper is from 20 to 60 wt % based on the entire amount of the hydrogenation catalyst, and in the calcium silicate, the molar ratio of calcium oxide (CaO) to silicon oxide ($SiO_2$) is less than 1.

7 Claims, 1 Drawing Sheet

(51) Int. Cl.
*B01J 21/16* (2006.01)
*B01J 35/10* (2006.01)

(56) References Cited

FOREIGN PATENT DOCUMENTS

| JP | 7-25795 | 1/1995 |
|---|---|---|
| JP | 9-124562 | 5/1997 |
| JP | 11-507867 | 7/1999 |
| JP | 2000-103966 | 4/2000 |
| JP | 2004-535470 | 11/2004 |
| JP | 2007-7520 | 1/2007 |
| JP | 2007-289855 | 11/2007 |

OTHER PUBLICATIONS

JP-11507867 machine translation (1999), pp. 1-14.*
JP-725795 machine translation (1995), pp. 1-10.*
JP-2007289855 machine translation, translation date: Dec. 15, 2014.*
JP-11507867 machine translation, translation date: Dec. 15, 2014.*
Extended European Search Report in EP 10 83 9583 dated Apr. 25, 2014.
International Search Report for PCT/JP2010/073414, mailed Apr. 5, 2011.
Gotti et al., "Basic Metal Oxides as Cocatalysts for Cu/Sio2 Catalysts in the Conversion of Synthesis Gas to Methanol", *J. Catal.*, vol. 178, No. 2, Sep. 10, 1998, pp. 511-519.
Dang et al., "Vapor-phase synthesis of isoprene from formaldehyde and isobutylene over CuSO4-MOx/SiO2 catalysts," *Reaction Kinetics and Catalysis Letters*, vol. 143, No. 2, Apr. 1991, pp. 495-500.
Koza, (Catalytic engineering course) 10, "Gensobetsu Shokubai Binran (Elemental Catalyst Handbook)", *Catalyst Society of Japan*, No Date, 4 pages, 1989.

\* cited by examiner

HYDROGENATION CATALYST, PROCESS FOR ITS PRODUCTION AND ITS USE

This application is the U.S. national phase of International Application No. PCT/JP2010/073414 filed 24 Dec. 2010 which designated the U.S. and claims priority to JP Patent Application Nos. 2009-295876 filed 25 Dec. 2009 and 2009-295877 filed 25 Dec. 2009, the entire contents of each of which are hereby incorporated by reference.

TECHNICAL FIELD

The present invention relates to a catalyst to be used for hydrogenation of organic compounds. Specifically, it relates to a useful catalyst to be used for hydrogenation of an aldehyde, a ketone, a carboxylic acid, a carboxylic acid ester, an aromatic nitro compound, etc.

BACKGROUND ART

As a useful catalyst to be used for such a hydrogenation reaction, a copper/chromium oxide catalyst has been widely known as a copper chromite catalyst (e.g. Non-Patent Document 1).

As a specific example, a process for producing aniline has been known wherein a gaseous nitrobenzene is reduced with hydrogen by means of a copper/chromium oxide catalyst under such conditions that the reaction temperature is from 180 to 370° C., the pressure is from 0.1 to 0.5 MPa and a nitrobenzene concentration is from 2 to 14 vol % (e.g. Patent Document 1). However, such a catalyst containing chromium oxide is likely to cause environmental contamination or health hazard, and a due care is required in its handling, and further, substantial labor and costs have been required also for the treatment and recovery of the catalyst used.

Further, a process for producing an aromatic amine by hydrogenation of an aromatic nitro compound by using a modified Raney copper which comprises copper, iron and aluminum as basic components, has been proposed (e.g. Patent Document 2). However, a Raney metal catalyst is usually susceptible to deterioration of the activity due to surface oxidation and is therefore required to be stored in water or in an inert gas atmosphere, and a due care is required for its handling. Further, while its activity is high, it has such a problem that the durability is inadequate.

Recently, a molded hydrogenation catalyst has been proposed which is made of a natural clay mineral such as copper, calcium silicate, attapulgite, etc. (e.g. Patent Document 3). While such a molded catalyst is excellent in strength and durability, it contains natural material as raw material, and it has a drawback that reproducibility is poor with respect to the composition or particle size of the catalyst to be produced, due to variations in its composition or physical properties.

Further, a molded catalyst comprising copper, calcium silicate, hydrotalcite, etc., has been proposed (e.g. Patent Document 4). However, such a molded catalyst employs hydrotalcite having the composition controlled, and petal-shaped calcium silicate, and therefore, it has an economical problem that the price is obliged to be relatively high.

PRIOR ART DOCUMENTS

Patent Documents

Patent Document 1: JP-A-49-231
Patent Document 2: JP-A-9-124562
Patent Document 3: JP-A-11-507867
Patent Document 4: JP-A-2007-289855

Non-Patent Document

Non-Patent Document 1: SHOKUBAI KOGAKU KOZA (Catalytic engineering course) 10 "GENSOBETSU SHOKUBAI BINRAN (Elemental Catalyst Handbook)", compiled by Catalyst Society of Japan (page 80)

DISCLOSURE OF INVENTION

Technical Problem

It is an object of the present invention to provide a catalyst which does not contain chromium oxide, unlike conventional copper/chromium oxide catalysts, and therefore does not cause any environmental contamination or health hazard, and which shows an activity, selectivity and durability at equivalent or higher levels to or than those of conventional copper/chromium oxide catalyst.

Solution to Problem

The present invention has been made as a result of an extensive study by the present inventors and provides the following.

1. A hydrogenation catalyst which comprises, as the main components, (1) copper and (2) at least one member selected from the group consisting of silicon oxide, calcium oxide and calcium silicate, wherein the content of the copper is from 20 to 60 wt % based on the entire amount of the hydrogenation catalyst, and in the calcium silicate, the molar ratio of calcium oxide (CaO) to silicon oxide ($SiO_2$) is less than 1.
2. The hydrogenation catalyst according to the above 1, which further contains an alkali metal in an amount of from 0.22 to 2.5 wt %, based on the entire amount of the hydrogenation catalyst.
3. The hydrogenation catalyst according to the above 1 or 2, wherein in the calcium silicate, the molar ratio of calcium oxide (CaO) to silicon oxide ($SiO_2$) is from 0.1 to 0.7.
4. The hydrogenation catalyst according to any one of the above 1 to 3, wherein the surface area of the calcium silicate is at least 100 $m^2/g$.
5. The hydrogenation catalyst according to any one of the above 2 to 4, wherein the alkali metal is sodium.
6. The hydrogenation catalyst according to any one of the above 1 to 5, which is used as a catalyst for hydrogenation of an aldehyde, a ketone, a carboxylic acid, a carboxylic acid ester or an aromatic nitro compound.
7. The hydrogenation catalyst according to the above 6, wherein the aromatic nitro compound is nitrobenzene.
8. A process for producing the hydrogenation catalyst as defined in the above 1, which comprises reducing, with hydrogen gas, a hydrogenation catalyst precursor comprising (1) a copper oxide in an amount of from 30 to 75 wt % based on the entire amount of the hydrogenation catalyst precursor and (2) at least one member selected from the group consisting of silicon oxide, calcium oxide and calcium silicate.
9. A process for producing the hydrogenation catalyst as defined in the above 2, which comprises reducing, with hydrogen gas, a hydrogenation catalyst precursor comprising (1) a copper oxide in an amount of from 30 to 75 wt % based on the entire amount of the hydrogenation catalyst precursor, (2) at least one member selected from the group consisting of silicon oxide, calcium oxide and calcium silicate and (3) an alkali metal in an amount of from 0.22 to 2.5 wt % based on the entire amount of the hydrogenation catalyst precursor.

10. A process for producing a hydrogenated compound, which comprises contacting and reducing at least one compound selected from the group consisting of an aldehyde, a ketone, a carboxylic acid, a carboxylic acid ester and an aromatic nitro compound with hydrogen within a temperature range of from 100 to 350° C. in the presence of the hydrogenation catalyst as defined in any one of the above 1 to 5.

11. The process for producing a hydrogenated compound according to the above 10, wherein the aromatic nitro compound is nitrobenzene, and the hydrogenated compound is aniline.

Advantageous Effects of Invention

The hydrogenation catalyst of the present invention does not contain hazardous chromium as a component and has an excellent activity, selectivity and long catalyst life for a hydrogenation reaction of an aldehyde, a ketone, a carboxylic acid, a carboxylic acid ester, an aromatic nitro compound, etc.

DESCRIPTION OF EMBODIMENTS

Figure 1:
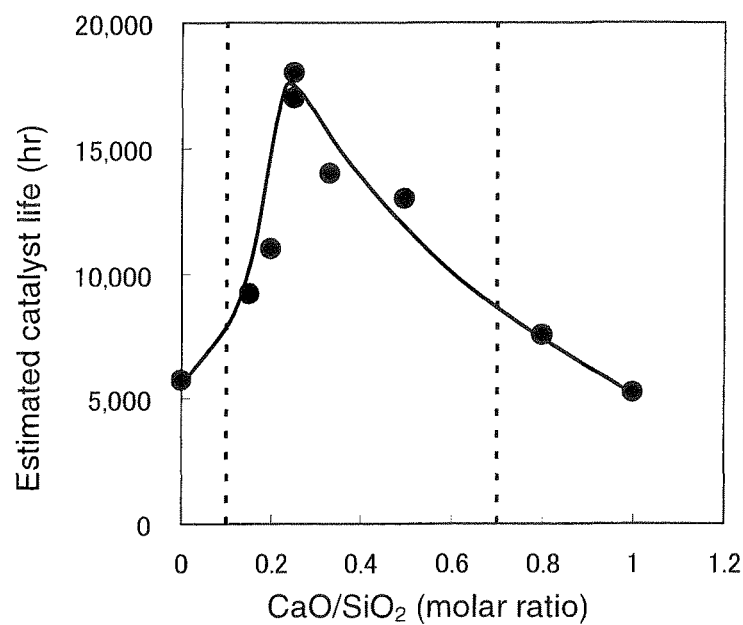
FIG. 1 shows the relation between the $CaO/SiO_2$ molar ratio in calcium silicate and the estimated catalyst life.

Now, the present invention will be described in detail.

The present invention provides a hydrogenation catalyst which comprises, as the main components, (1) copper and (2) at least one member selected from the group consisting of silicon oxide, calcium oxide and calcium silicate, in a total amount of preferably at least 90 wt %, particularly preferably at least 95 wt %, wherein the content of the copper is from 20 to 60 wt % based on the entire amount of the hydrogenation catalyst, and in the calcium silicate, the molar ratio of calcium oxide (CaO) to silicon oxide ($SiO_2$) is less than 1. Further, the present invention provides such a hydrogenation catalyst which further contains an alkali metal in an amount of from 0.22 to 2.5 wt %, based on the entire amount of the hydrogenation catalyst.

The copper as a component of the hydrogenation catalyst is prepared by reducing a hydrogenation catalyst precursor containing copper oxide, a hydroxide, carbonate or nitrate which can readily be converted to copper oxide by firing, or a mixture of two or more of them. The hydrogenation catalyst of the present invention contains the copper in an amount of from 20 to 60 wt %, preferably from 30 to 60 wt %, more preferably from 30 to 55 wt %, based on the entire amount of the hydrogenation catalyst. If the content of the copper is less than 20 wt %, the activity tends to be deficient to the reaction load (the raw material-feeding amount), whereby coking tends to increase, and the catalyst life (useful life) tends to be short. On the other hand, if the content of the copper exceeds 60 wt %, the dispersibility at the time of supporting the copper tends to deteriorate, and the activity per the supported copper tends to be low. Further, the content of the copper is preferably within a range of from 30 to 60 wt %, more preferably from 30 to 55 wt %, whereby improvement of the catalyst life can be expected.

The content of the copper in the hydrogenation catalyst was calculated as copper ions by a method in accordance with the ICP analytical method disclosed in JIS K0400-52-30.

Among silicon oxide, calcium oxide and calcium silicate to be used in the present invention, calcium silicate is most preferred, and it may be either natural one or synthetic one. In the calcium silicate, the molar ratio of calcium oxide (CaO) to silicon oxide ($SiO_2$) is preferably less than 1, more preferably within a range of from 0.1 to 0.7, most preferably within a range of from 0.2 to 0.4. When the molar ratio of CaO calculated as calcium oxide to $SiO_2$ calculated as silicon oxide, in the calcium silicate, is less than 1, preferably within a range of from 0.1 to 0.7, the dispersibility of copper at the time of supporting the copper will be remarkably high, and the supported copper particles will be fine particles. As a result, the surface area of the copper increases to bring about an effect to increase the catalyst activity. Further, the acidity/basicity of the catalyst is thereby modified to bring about an effect to prevent so-called coking i.e. precipitation of carbon on the catalyst surface. Thus, it is considered that deterioration of the activity by coking is prevented, and the catalyst life is substantially prolonged. Further, when the molar ratio of calcium oxide (CaO) to silicon oxide ($SiO_2$) in the calcium silicate is within a range of from 0.2 to 0.4, further improvement of the catalyst life is expected, such being desirable.

In the present invention, silicon oxide ($SiO_2$) in the calcium silicate was calculated by a method in accordance with the gravimetric method disclosed in JIS K0101, and calcium oxide (CaO) was calculated as calcium ions by a method in accordance with the ICP analytical method disclosed in JIS K0400-52-30 and converted to calcium oxide.

The surface area of the calcium silicate to be used in the present invention is preferably at least 100 $m^2/g$, more preferably at least 150 $m^2/g$. When the surface area of the calcium silicate is at least 100 $m^2/g$, copper will be supported, as highly dispersed, on the calcium silicate. Accordingly, copper particles will be fine particles, and as a result, the surface area of the copper becomes large to bring about an effect to increase the catalyst activity. It is considered that coking is thereby prevented, and the catalyst life is substantially prolonged. Further, when the surface area of the calcium silicate is at least 150 $m^2/g$, further improvement of the catalyst life is expected, such being desirable.

The surface area of the calcium silicate was calculated by a method in accordance with the gas adsorption method disclosed in JIS Z8830.

The calcium silicate to be used in the present invention may be either the natural one or synthetic one, but it is preferred to employ one synthesized by controlling the molar ratio of calcium oxide (CaO) to silicon oxide ($SiO_2$) to be from 0.1 to 0.7.

More specifically, silicon oxide and a calcium source reactive therewith, such as quick lime (calcium oxide), slaked lime (calcium hydroxide), calcium chloride or calcium carbonate, are mixed under the atmospheric pressure at room temperature or under heating to obtain calcium silicate. At that time, an alkali such as sodium hydroxide or sodium carbonate may be added to accelerate the reaction. The silicon oxide may be crystalline or non-crystalline or a mixture thereof, but non-crystalline one is preferred. Such non-crystalline silicon oxide may be one produced by either a dry synthetic method or a wet synthetic method. However, inexpensive one produced by a wet synthetic method is available as a commercial product, for example, Nipsil "NS-K" (registered trademark) manufactured by TOSOH SILICA CORPORATION.

The hydrogenation catalyst of the present invention may contain an alkali metal in an amount of from 0.22 to 2.5 wt %, preferably from 0.25 to 1.7 wt %, based on the entire amount of the hydrogenation catalyst. The alkali metal may be present in the form of reduced metal, in the form of an oxide or in a form which can be converted to the oxide. By incorporating from 0.22 to 2.5 wt % of an alkali metal, particularly sodium, to the hydrogenation catalyst of the present invention in such a manner, the acidity/basicity of the catalyst is modified to obtain an effect to prevent so-called coking i.e. precipitation of carbon on the catalyst surface. It is considered that as a result, deterioration of the activity by coking is prevented, and the catalyst life is substantially prolonged. Further, when the content of the alkali metal is within a range of from 0.25 to 1.7 wt %, further improvement of the catalyst life is expected, such being desirable.

Here, the content of the alkali metal in the hydrogenation catalyst is one measured and obtained as alkali metal ions by a method in accordance with the ICP analytical method disclosed in JIS K0400-52-30.

At the time of producing the catalyst of the present invention, a means to mix calcium silicate and copper, or copper oxide or at least one copper compound which can readily be converted to copper oxide by firing such as a hydroxide, carbonate or nitrate, is not particularly limited, and any means may be employed so long as it is a means capable of uniformly mixing them. For example, such a composition is charged into a mixing apparatus and subjected to dry mixing or wet mixing, and the obtained mixture is dried and fired to obtain a precursor powder for the hydrogenation catalyst of the present invention.

Otherwise, to an aqueous slurry of the above-mentioned calcium silicate wet-synthesized from silicon oxide and calcium oxide, an aqueous solution of e.g. copper nitrate or copper chloride is added continuously, dividedly or all at once, followed by neutralization with e.g. an aqueous sodium hydroxide solution, an aqueous sodium carbonate solution or an aqueous sodium hydrogencarbonate solution to have copper supported on calcium silicate, followed by filtration to obtain a catalyst wet cake. The obtained wet cake is dried to obtain a precursor powder for the hydrogenation catalyst of the present invention.

Using a flowability-adjusting agent, a pore-imparting agent, a reinforcing agent or a binder such as clay, as an adjuvant, as the case requires, the powdery catalyst is subjected to extrusion molding or compression molding to obtain a molded product of a various structure or shape, followed by firing to obtain a molded product of the hydrogenation catalyst precursor.

In the present invention, the hydrogenation catalyst precursor is reduced and activated to form a hydrogenation catalyst, preferably in the reactor, before carrying out the intended hydrogenation reaction. As a method for reducing the hydrogenation catalyst precursor, for example, in a case where the reduction is carried out in a gas phase or liquid phase by using hydrogen gas as a reducing agent, it is preferred to carry out gas phase reduction at a temperature of from 100 to 500° C., preferably from 150 to 300° C. If the temperature is less than 100° C., the reduction reaction tends to hardly proceed, and if it exceeds 500° C., deterioration of the activity is likely to occur due to sintering of copper, such being undesirable. Further, within a temperature range of from 150 to 300° C., the reaction proceeds under a stabilized condition, such being preferred. In such a case, hydrogen gas diluted with an inert gas such as nitrogen, helium or argon may be used.

The hydrogenation catalyst of the present invention thus obtained is useful for a hydrogenation reaction of an aldehyde, a ketone, a carboxylic acid, a carboxylic acid ester or an aromatic nitro compound.

The aldehyde which can be hydrogenated by means of the catalyst of the present invention to produce an alcohol may, for example, be formaldehyde, propionaldehyde, n-butyraldehyde, isobutyraldehyde, valeraldehyde, 2-methylbutyraldehyde, 3-methylbutyraldehyde, 2,2-dimethylpropionaldehyde, capronaldehyde, 2-methylvaleraldehyde, 3-methylvaleraldehyde, 4-methylvaleraldehyde, 2-ethylbutyraldehyde, 2,2-dimethylbutyraldehyde, 3,3-dimethylbutyraldehyde, caprylaldehyde, capric aldehyde or glutardialdehyde. The ketone may, for example, be acetone, butanone, pentanone, hexanone, cyclohexanone or acetophenone.

The carboxylic acid or carboxylic acid ester which can be hydrogenated by means of the catalyst of the present invention to produce an alcohol, may, for example, be formic acid, acetic acid, capronic acid, caprylic acid, lauric acid, myristic acid, palmitic acid, stearic acid, isostearic acid, oleic acid, oxalic acid, maleic acid, adipic acid, sebacic acid, cyclohexanecarboxylic acid, benzoic acid or phthalic acid, or an ester thereof.

The aromatic nitro compound which can be hydrogenated by means of the catalyst of the present invention to produce an aromatic amine compound, may, for example, be nitrobenzene, an alkyl-substituted nitrobenzene, a nitronaphthalene, 4-nitrodiphenyl, nitroanthraquinone, a nitrophenanthro, 2-nitrofuran, 2-nitrothiophene, 3-nitropyridine, 2-nitrodiphenyl ether, 5-nitro-1H-benzotriazole, an isomeric dinitrobenzene, an isomeric nitroaniline, p-nitrobenzoic acid, m-nitrobenzoic acid, o-nitrobenzoic acid, an isomeric nitrophenol, o-nitrochlorobenzene, m-nitrochlorobenzene, p-nitrochlorobenzene or 3,4-dinitrochlorobenzene. Particularly, nitrobenzene is a nitro compound to which the hydrogenation reaction of the present invention may suitably be applied.

The hydrogenation of nitrobenzene is carried out usually at a temperature within a range of from 100 to 350° C. under a pressure of from 0.1 to 0.5 MPa, whereby side reactions can be suppressed, and the catalyst life can be prolonged. The molar ratio of hydrogen/nitrobenzene is preferably from 10 to 20, and with a view to removing a reaction heat or preventing the catalyst deterioration, the reaction may be carried out by mixing an inert gas such as nitrogen. GHSV (gas hourly space velocity) is preferably within a range of 1,000 to 2,000 $h^{-1}$.

EXAMPLES

Now, the present invention will be described in detail with reference to Examples, but it should be understood that the present invention is by no means limited by such Examples.

Example 1

(Preparation of Molded Hydrogenation Catalyst Precursor)

Into a 2 L glass container, 225 mL of ion exchanged water was added, and then, 30.0 g of silica powder (Nipsil "NS-K", manufactured by TOSOH SILICA CORPORATION) and 7.0 g of quick lime powder (Reagent grade 1, manufactured by KANTO CHEMICAL CO., INC.) were charged so that the molar ratio ($CaO/SiO_2$ molar ratio) of calcium oxide to silica (silicon oxide) would be 0.25, followed by stirring for 24 hours at 25° C. to prepare a calcium silicate carrier. While maintaining the aqueous calcium silicate slurry thus prepared, at 25° C. with stirring, 382.7 g of a 39 wt % copper nitrate aqueous solution (manufactured by KANSAI CATALYST CO., LTD.) was added at a constant speed over 3 hours.

At that time, the aqueous slurry was adjusted to a pH of from 6.5 to 7.5 with a 20 wt % sodium carbonate aqueous solution. After completion of the addition of the copper nitrate aqueous solution, stirring and aging were carried out at 25° C. for 2 hours. Then, the precipitate was collected by filtration, and the wet cake was washed with 3 L of ion exchanged water.

The obtained wet cake was dried in air overnight at 110° C., and the dried solid was roughly pulverized and fired at 450° C. for 3 hours. To the obtained fired powder, 2.0 g of graphite was added and mixed as a lubricant, followed by molding into a cylindrical shape of 5 mm in diameter×5 mm by a rotary tabletting machine. The obtained molded product was again fired at 450° C. for 3 hours to obtain a molded hydrogenation catalyst precursor.

(Hydrogenation Reaction of Nitrobenzene)

The above molded hydrogenation catalyst precursor was pulverized by a mortar, and by means of sieves with mesh sizes of 2.8 mm and 1.0 mm, the catalyst was sieved to obtain particles of from 2.8 to 1.0 mm. 30 mL of the sieved catalyst particles were packed into a fixed bed reactor made of SUS and reduced (at 215° C. for 24 hours) in a hydrogen stream and activated. For evaluation of the catalytic performance, a hydrogenation reaction of nitrobenzene was continuously carried out for 800 hours under such conditions that the hydrogen pressure was 0.14 MPa, the reaction temperature was 175° C., GHSV was 1,500 $h^{-1}$, LHSV (liquid hourly space velocity) was 0.4 $h^{-1}$ and the hydrogen/nitrobenzene molar ratio was 15. The obtained reaction products were analyzed by gas chromatography (apparatus: GC-14A manufactured by Shimadzu Corporation, column: DB170). The aniline selectivity after the reaction for 800 hours was 99.8%. Further, the estimated catalyst life calculated from the moving rate of the maximum temperature position in the catalyst layer during this reaction for 800 hours was about 17,000 hours.

In Table 1, the copper content (wt %), the $CaO/SiO_2$ molar ratio, the aniline selectivity (%) after the reaction for 800 hours and the estimated catalyst life (hours) are shown.

Here, the content of the copper was quantitatively analyzed by ICP Optima 5300DV manufactured by PerkinElmer. Further, the carrier surface area was measured by FlowSorb II2300, manufactured by Shimadzu Corporation.

Examples 2 to 5

The preparation of the molded hydrogenation catalyst precursor and the hydrogenation reaction of nitrobenzene were carried out in the same manner as in Example 1 except that the copper content (wt %) and the $CaO/SiO_2$ molar ratio were changed to the prescribed levels shown in Table 1. The results of the aniline selectivity after the reaction for 800 hours and the estimated catalyst life are shown in Table 1.

Example 6

(Preparation of Molded Hydrogenation Catalyst Precursor)

Into a 2 L glass container, 225 mL of ion exchanged water was added, and then, 36.0 g of silica powder (Nipsil "NS-K", manufactured by TOSOH SILICA CORPORATION) and 11.1 g of slaked lime powder (Reagent grade 1, manufactured by KANTO CHEMICAL CO., INC.) were charged so that the molar ratio ($CaO/SiO_2$ molar ratio) of calcium oxide to silica (silicon oxide) would be 0.25, followed by stirring for 6 hours at 40° C. to prepare a calcium silicate carrier. While maintaining the prepared aqueous calcium silicate slurry at 40° C. with stirring, 305.5 g of a 39 wt % copper nitrate aqueous solution (manufactured by KANSAI CATALYST CO., LTD.) was added at a constant speed over 4 hours. At that time, the aqueous slurry was adjusted to a pH of from 6.5 to 7.5 with a 20 wt % sodium carbonate aqueous solution. After completion of the addition of the copper nitrate aqueous solution, stirring and aging were carried out at 40° C. for 2 hours. Then, the precipitate was collected by filtration, and the wet cake was washed with 3 L of ion exchanged water.

The obtained wet cake was dried in air overnight at 110° C. To the obtained dry powder, 2.0 g of graphite was added and mixed as a lubricant, followed by molding into a cylindrical shape of 5 mm in diameter×5 mm by a rotary tabletting machine. The obtained molded product was again fired at 450° C. for 3 hours to obtain a molded hydrogenation catalyst precursor.

(Hydrogenation Reaction of Nitrobenzene)

The reaction was carried out in the same manner as in Example 1 except that the obtained molded hydrogenation catalyst precursor was used. The results of the aniline selectivity after the reaction for 800 hours and the estimated catalyst life are shown in Table 1.

Examples 7 and 8

The operation was carried out in the same manner as in Example 6 except that the copper content (wt %) and the $CaO/SiO_2$ molar ratio were changed to the prescribed levels shown in Table 1. The results of the aniline selectivity after the reaction for 800 hours and the estimated catalyst life are shown in Table 1.

Example 9

The operation was carried out in the same manner as in Example 6 except that as the silica component, silica powder (Nipgel "CX-200", manufactured by TOSOH SILICA CORPORATION) was used, and the copper content (wt %) and the $CaO/SiO_2$ molar ratio were changed to the prescribed levels shown in Table 1. The results of the aniline selectivity after the reaction for 800 hours and the estimated catalyst life are shown in Table 1.

Example 10

The operation was carried out in the same manner as in Example 6 except that calcium silicate having a surface area of 130 $m^2/g$ (Fluorite, manufactured by Tokuyama Corporation) was used, and the $CaO/SiO_2$ molar ratio and the copper content (wt %) were changed to the prescribed levels shown in Table 1. The results of the aniline selectivity after the reaction for 800 hours and the estimated catalyst life are shown in Table 1.

Comparative Examples 1 to 3

The operation was carried out in the same manner as in Example 1 except that the copper content (wt %) and the $CaO/SiO_2$ molar ratio were changed to the prescribed levels shown in Table 1. The results of the aniline selectivity after the reaction for 800 hours and the estimated catalyst life are shown in Table 1.

Comparative Example 4

(Preparation of Molded Hydrogenation Catalyst Precursor)

Into a 2 L glass container, 400 mL of ion exchanged water was charged, and with stirring, 286 mL of sodium silicate No. 3 liquid (manufactured by KISHIDA CHEMICAL Co., Ltd.)

having a silica content of 6.76 mol/L and 302 mL of a 0.16 mol/L aluminum sulfate aqueous solution (manufactured by KANTO CHEMICAL CO., INC.) were, respectively, introduced at a constant speed for 1 hour by means of metering pumps. Such a reaction operation was carried out at 25° C., and the pH after completion of the reaction became 4. Then, the obtained reaction solution was heated and aged at 95° C. for 1 hour.

Then, suction filtration was carried out using Nutsche, and the obtained wet cake was washed with 500 mL of ion exchanged water. The obtained wet cake was dried in air at 75° C. overnight, and the obtained solid was roughly pulverized to obtain an aluminum silicate carrier.

Into a 2 L glass container, 400 mL of ion exchanged water was added, and then, 32 g of the above aluminum silicate carrier was added, followed by heating to 60° C. To the aqueous carrier slurry thus prepared, 382.7 g of a 39 wt % copper nitrate aqueous solution (manufactured by KANTO CHEMICAL CO., INC.) was added at a constant speed over 3 hours with stirring while maintaining the temperature at 60° C. At that time, the aqueous slurry was adjusted to a pH of from 6.5 to 7.5 with a 20 wt % sodium carbonate aqueous solution. After completion of the addition of the aqueous copper nitrate solution, aging was carried out for 2 hours at 60° C. Then, the precipitate was collected by filtration, and the wet cake was washed with 3 L of ion exchanged water.

The obtained wet cake was dried in air at 110° C. overnight. This dried solid was roughly pulverized and fired at 450° C. for 3 hours. To the obtained fired powder, 5 g of silica sol (SNOWTEX 40, manufactured Nissan Chemical Industries, Ltd.) was added and mixed as a binder, followed by molding into a cylindrical shape of 5 mm in diameter×5 mm by a rotary tableting machine. The obtained molded product was again fired at 450° C. for 3 hours to obtain a molded hydrogenation catalyst precursor.
(Hydrogenation Reaction of Nitrobenzene)

The operation was carried out in the same manner as in Example 1 except that the obtained molded hydrogenation catalyst precursor was used. The results of the aniline selectivity after the reaction for 800 hours and the estimated catalyst life are shown in Table 1.

Comparative Example 5

(Preparation of Molded Hydrogenation Catalyst Precursor)

Into a 2 L glass container, 1 L of ion exchanged water was added, and then, 111.2 g of copper nitrate trihydrate (special grade reagent, manufactured by KANTO CHEMICAL CO., INC.) was added. The temperature was raised to 80° C. with stirring to prepare a copper nitrate aqueous solution. Separately, to 0.8 L of ion exchanged water, 45 g of sodium hydroxide (Reagent grade 1, manufactured by KANTO CHEMICAL CO., INC.) was added and dissolved to prepare a sodium hydroxide aqueous solution. While maintaining the above copper nitrate aqueous solution at 80° C. with stirring, the sodium hydroxide aqueous solution was added. After completion of the addition, stirring was carried out at 80° C. for 30 minutes, and then, the slurry was cooled to 50° C. The precipitate was collected by filtration, and the wet cake was washed with 366 mL of ion exchanged water.

Then, into a 2 L glass container, 1 L of ion exchanged water was added, and the above precipitate was added and repulped. Further, 40.2 g of calcium silicate (Fluorite, manufactured by Tokuyama Corporation) and 1.8 g of hydrotalcite (ALCAMAC, manufactured by Kyowa Chemical Industry Co., Ltd.) containing magnesium, were added, followed by stirring for 1 hour. Such a slurry was filtered to obtain a wet cake.

The obtained wet cake was dried in air at 110° C. overnight. The dried solid was roughly pulverized. To the obtained dry powder, 1.5 g of graphite was added and mixed as a lubricant, followed by molding by a press molding machine. This molded product was fired at 400° C. for 6 hours to obtain a molded hydrogenation catalyst precursor.
(Hydrogenation Reaction of Nitrobenzene)

The reaction was carried out in the same manner as in Example 1 except that the obtained molded hydrogenation catalyst precursor was used. The results of the aniline selectivity after the reaction for 800 hours and the estimated catalyst life are shown in Table 1.

Comparative Example 6

(Preparation of Molded Hydrogenation Catalyst Precursor)

Into a 2 L glass container, 1 L of ion exchanged water was added, and then, 111.2 g of copper nitrate trihydrate (special reagent grade, manufactured by KANTO CHEMICAL CO., INC.) was added. The temperature was raised to 80° C. with stirring to prepare a copper nitrate aqueous solution. Separately, to 0.8 L of ion exchanged water, 45 g of sodium hydroxide (Reagent grade 1, manufactured by KANTO CHEMICAL CO., INC.) was added and dissolved to prepare a sodium hydroxide aqueous solution. While maintaining the above copper nitrate aqueous solution at 80° C. with stirring, the sodium hydroxide aqueous solution was added. After completion of the addition, stirring was carried out at 80° C. for 30 minutes, and then, the slurry was cooled to 50° C. The precipitate was collected by filtration, and the wet cake was washed with 366 mL of ion exchanged water. The obtained wet cake was dried at 110° C. overnight to obtain cupric oxide powder.

Into a mortar, 25.7 g of this cupric oxide powder, 9.1 g of calcium hydroxide (Reagent grade 1, manufactured by KANTO CHEMICAL CO., INC.) and 2.1 g of attapulgite clay (Attagel 40, manufactured by BASF) were added and kneaded for 5 minutes. Then, 28.9 g of 40 wt % colloidal silica (SNOWTEX 40, manufactured by Nissan Chemical Industries, Ltd.) was added, followed by kneading for 27 minutes. Further, while adding 9.0 mL of ion exchanged water, kneading was continued for 34 minutes.

The obtained kneaded product was molded by a press-molding machine and dried in air at 125° C. overnight. This dried molded product was fired at 600° C. for 2 hours to obtain a molded hydrogenation catalyst precursor.
(Hydrogenation Reaction of Nitrobenzene)

The reaction was carried out in the same manner as in Example 1 except that the obtained molded hydrogenation catalyst precursor was used. The results of the aniline selectivity after the reaction for 800 hours and the estimated catalyst life are shown in Table 1.

TABLE 1

| | Cu (wt %) | $CaO/SiO_2$ molar ratio in carrier | Surface area of carrier ($m^2/g$) | Aniline selectivity (%) | Estimated catalyst life (hr) |
|---|---|---|---|---|---|
| Ex. 1 | 52.2 | 0.25 | 290 | 99.8 | 17,000 |
| Ex. 2 | 50.0 | 0.15 | | 99.8 | 9,200 |
| Ex. 3 | 51.1 | 0.5 | 275 | 99.8 | 13,000 |
| Ex. 4 | 49.8 | 0.33 | | 99.5 | 14,000 |
| Ex. 5 | 50.8 | 0.2 | | 99.5 | 11,000 |
| Ex. 6 | 39.5 | 0.25 | 290 | 99.8 | 16,000 |
| Ex. 7 | 36.0 | 0.25 | | 99.8 | 17,000 |
| Ex. 8 | 23.7 | 0.25 | | 99.9 | 9,700 |
| Ex. 9 | 47.1 | 0.25 | 625 | 99.7 | 18,000 |

TABLE 1-continued

|  | Cu (wt %) | CaO/SiO$_2$ molar ratio in carrier | Surface area of carrier (m$^2$/g) | Aniline selectivity (%) | Estimated catalyst life (hr) |
|---|---|---|---|---|---|
| Ex. 10 | 48.5 | 0.30 | 130 | 99.8 | 8,600 |
| Comp. Ex. 1 | 51.3 | 1.0 |  | 99.8 | 5,900 |
| Comp. Ex. 2 | 50.9 | 0 | 214 | 99.8 | 5,700 |
| Comp. Ex. 3 | 49.4 | 0.8 |  | 99.7 | 7,500 |
| Comp. Ex. 4 | 49.9 |  |  | 99.9 | 2,500 |
| Comp. Ex. 5 | 42.7 | 0.30 | 130 | 99.7 | 5,000 |
| Comp. Ex. 6 | 38.6 | 0.64 |  | 99.8 | 7,900 |

Example 11

(Preparation of Molded Hydrogenation Catalyst Precursor)

Into a 2 L glass container, 225 mL of ion exchanged water was added, and then, 30.0 g of silica powder (Nipsil "NS-K", manufactured by TOSOH SILICA CORPORATION) and 7.0 g of quick lime powder (Reagent grade 1, manufactured by KANTO CHEMICAL CO., INC.) were charged so that the molar ratio (CaO/SiO$_2$ molar ratio) of calcium oxide to silica (silicon oxide) would be 0.25, followed by stirring at 25° C. for 24 hours to prepare a calcium silicate carrier. To the aqueous calcium silicate slurry thus prepared, 382.7 g of a 39 wt % copper nitrate aqueous solution (manufactured by KANSAI CATALYST CO., LTD.) was added at a constant speed over 3 hours while maintaining the temperature at 25° C. with stirring. At that time, the aqueous slurry was adjusted to a pH of from 6.5 to 7.5 with a 20 wt % sodium carbonate aqueous solution. After completion of the addition of the copper nitrate aqueous solution, stirring and aging were carried out for 2 hours at 25° C. Then, the precipitate was collected by filtration, and the wet cake was washed with 5 L of ion exchange water.

The obtained wet cake was dried in air at 110° C. overnight, and the dried solid was roughly pulverized and fired at 450° C. for 3 hours. To the obtained fired powder, 2.0 g of graphite was added and mixed as a lubricant, followed by molding into a cylindrical shape of 5 mm in diameter×5 mm by a rotary tableting machine. The obtained molded product was again fired at 450° C. for 3 hours to obtain a molded hydrogenation catalyst precursor. The sodium content in this molded catalyst precursor was 0.26 wt %.

Here, the content of sodium was measured by ICP Optima 5300DV, manufactured by PerkinElmer.

(Hydrogenation Reaction of Nitrobenzene)

The above molded hydrogenation catalyst precursor was pulverized by a mortar, and using sieves with mesh sizes of 2.8 mm and 1.0 mm, the catalyst was sieved to obtain particles of from 2.8 to 1.0 mm. 30 mL of the sieved catalyst particles were packed into a fixed bed reactor made of SUS and reduced (at 215° C. for 24 hours) in a hydrogen stream and activated. For evaluation of the catalytic performance, a hydrogenation reaction of nitrobenzene was continuously carried out for 800 hours under such conditions that the hydrogen pressure was 0.14 MPa, the reaction temperature was 175° C., GHSV was 1,500 h$^{-1}$, LHSV (liquid hourly space velocity) was 0.4 h$^{-1}$ and the hydrogen/nitrobenzene molar ratio was 15. The obtained reaction products were analyzed by gas chromatography. The aniline selectivity after the reaction for 800 hours was 99.6%. Further, the estimated catalyst life calculated from the moving rate of the maximum temperature position in the catalyst layer during this reaction for 800 hours, was about 13,000 hours.

In Table 2, the copper content (wt %), the CaO/SiO$_2$ molar ratio, the sodium content (wt %), the aniline selectivity (%) after the reaction for 800 hours and the estimated catalyst life (hours) are shown.

The measurement of the content of copper was carried out in the same manner as in Example 1.

Examples 12 to 17

The preparation of the molded hydrogenation catalyst precursor and the hydrogenation reaction of nitrobenzene were carried out in the same manner as in Example 11 except that the copper content (wt %) and the CaO/SiO$_2$ molar ratio were changed to the prescribed levels shown in Table 2. That is, the aqueous slurry was filtered, and the wet catalyst was washed by changing the amount of washing water so that the contained sodium became the prescribed content. The obtained wet cake was subjected to the same operation as in Example 11 to prepare the hydrogenation catalyst. The results of the aniline selectivity after the reaction for 800 hours and the estimated catalyst life are shown in Table 2.

Comparative Examples 7 to 8

The preparation of the molded hydrogenation catalyst precursor and the hydrogenation reaction of nitrobenzene were carried out in the same manner as in Example 11 except that the copper content (wt %) and the CaO/SiO$_2$ molar ratio became the prescribed levels shown in Table 2. That is, the aqueous slurry was filtered, and the wet catalyst was washed by changing the amount of washing water so that the contained sodium became the prescribed content. The obtained wet cake was subjected to the same operation as in Example 11 to prepare the hydrogenation catalyst. The results of the aniline selectivity after the reaction for 800 hours and the estimated catalyst life are shown in Table 2.

TABLE 2

|  | Cu (wt %) | CaO/SiO$_2$ molar ratio | Na (wt %) | Aniline selectivity (%) | Estimated catalyst life (hr) |
|---|---|---|---|---|---|
| Ex. 11 | 51.4 | 0.25 | 0.26 | 99.6 | 13,000 |
| Ex. 12 | 50.9 | 0.25 | 0.37 | 99.2 | 17,000 |
| Ex. 13 | 51.0 | 0.25 | 0.52 | 99.5 | 18,000 |
| Ex. 14 | 52.2 | 0.25 | 0.85 | 99.8 | 17,000 |
| Ex. 15 | 48.8 | 0.25 | 1.19 | 99.5 | 15,000 |
| Ex. 16 | 50.0 | 0.5 | 0.25 | 99.8 | 14,000 |
| Ex. 17 | 62.2 | 0.5 | 1.66 | 99.9 | 13,000 |
| Comp. Ex. 7 | 51.6 | 0.25 | 0.20 | 99.7 | 6,600 |
| Comp. Ex. 8 | 51.4 | 0.25 | 2.82 | 99.8 | 6,600 |

As is evident from the results shown in Tables 1 and 2, when the hydrogenation catalyst of the present invention is used, it is possible to obtain the product by hydrogenation at a high selectivity and in good yield, and further, the reaction can be continued over a remarkably long period of time.

Figure 2:
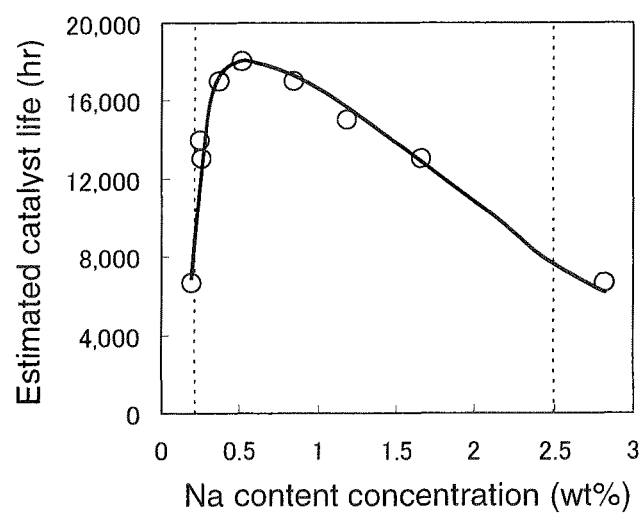
FIG. 2 shows the relation between the sodium content in the catalyst and the estimated catalyst life.

FIG. 1 shows the relation between the CaO/SiO$_2$ molar ratio in calcium silicate and the estimated catalyst life, and FIG. 2 shows the relation between the sodium content in the catalyst and the estimated catalyst life. As is evident from these relations, it is evident that when the hydrogenation catalyst of the present invention is used, it is possible to continue the hydrogenation reaction over a remarkably long period of time.

INDUSTRIAL APPLICABILITY

The hydrogenation catalyst according to the present invention does not contain hazardous chromium as a component and has an excellent activity, selectivity and long catalyst life for a hydrogenation reaction of an aldehyde, a ketone, a carboxylic acid, a carboxylic acid ester, an aromatic nitro compound, etc., and thus it is useful for a wide range of hydrogenation reactions of an aldehyde, a ketone, a carboxylic acid, a carboxylic acid ester, an aromatic nitro compound, etc.

The entire disclosures of Japanese Patent Application No. 2009-295876 filed on Dec. 25, 2009 and Japanese Patent Application No. 2009-295877 filed on Dec. 25, 2009 including specifications, claims, drawings and summaries are incorporated herein by reference in their entireties.

The invention claimed is:

1. A hydrogenation catalyst for hydrogenation of an aromatic nitro compound which consists of:
   (1) copper of from 20 to 60 wt % based on the entire amount of the hydrogenation catalyst,
   (2) calcium silicate at least 100 m²/g, and
   (3) an alkali metal in an amount of from 0.22 to 2.5 wt %, based on the entire amount of the hydrogenation catalyst and in the calcium silicate, the molar ratio of calcium oxide (CaO) to silicon oxide (SiO$_2$) is from 0.1 to 0.7.

2. The hydrogenation catalyst according to claim 1, wherein the alkali metal is sodium.

3. A process for producing the hydrogenation catalyst as defined in claim 1, which comprises reducing, with hydrogen gas, a hydrogenation catalyst precursor comprising (1) a copper oxide in an amount of from 30 to 75 wt % based on the entire amount of the hydrogenation catalyst precursor and (2) at least one member selected from the group consisting of silicon oxide, calcium oxide and calcium silicate.

4. A process for producing the hydrogenation catalyst as defined in claim 1, which comprises reducing, with hydrogen gas, a hydrogenation catalyst precursor comprising (1) a copper oxide in an amount of from 30 to 75 wt % based on the entire amount of the hydrogenation catalyst precursor, (2) at least one member selected from the group consisting of silicon oxide, calcium oxide and calcium silicate and (3) an alkali metal in an amount of from 0.22 to 2.5 wt % based on the entire amount of the hydrogenation catalyst precursor.

5. A process for producing a hydrogenated compound, which comprises contacting and reducing at least one compound selected from the group consisting of an aldehyde, a ketone, a carboxylic acid, a carboxylic acid ester and an aromatic nitro compound with hydrogen within a temperature range of from 100 to 350° C. in the presence of the hydrogenation catalyst as defined in claim 1.

6. The process for producing a hydrogenated compound according to claim 5, wherein the aromatic nitro compound is nitrobenzene.

7. The process for producing a hydrogenated compound according to claim 5, wherein the aromatic nitro compound is nitrobenzene, and the hydrogenated compound is aniline.

* * * * *